United States Patent [19]
Won et al.

[11] Patent Number: 5,955,109
[45] Date of Patent: Sep. 21, 1999

[54] METHODS AND COMPOSITIONS FOR TOPICAL DELIVERY OF RETINOIC ACID

[75] Inventors: Richard Won, Palo Alto; Martin A. Katz, Menlo Park; Chung H. Cheng, San Jose; Sergio Nacht, Los Altos, all of Calif.

[73] Assignee: Advanced Polymer Systems, Inc., Redwood City, Calif.

[21] Appl. No.: 08/079,220

[22] Filed: Jun. 17, 1993

Related U.S. Application Data

[63] Continuation of application No. 07/802,664, Dec. 5, 1991, abandoned, which is a continuation-in-part of application No. 07/644,869, Jan. 23, 1991, Pat. No. 5,145,675, which is a continuation of application No. 07/334,051, Apr. 5, 1989, abandoned, which is a division of application No. 07/091,641, Aug. 31, 1987, abandoned, which is a continuation-in-part of application No. 06/810,478, Dec. 18, 1985, abandoned, application No. 06/846,321, Mar. 31, 1986, abandoned, application No. 06/896,956, Aug. 15, 1986, abandoned, application No. 06/925,081, Oct. 30, 1986, abandoned, application No. 06/925,082, Oct. 30, 1986, abandoned, application No. 06/932,613, Nov. 11, 1986, abandoned, application No. 06/933,243, Nov. 21, 1986, abandoned, application No. 06/936,520, Dec. 1, 1986, abandoned, and application No. 06/940,754, Dec. 10, 1986, abandoned.

[51] Int. Cl.⁶ ..................................................... A61K 9/16
[52] U.S. Cl. .......................... 424/501; 514/951; 514/859
[58] Field of Search .............................. 424/78.31, 78.32, 424/78.03, 78.06, 501, 486, 487, 69, DIG. 13, 59; 514/772.4–772.6, 844–848, 859, 951, 965

[56] References Cited

U.S. PATENT DOCUMENTS

| | | | |
|---|---|---|---|
| 3,055,297 | 9/1962 | Leeds | 101/327 |
| 3,732,865 | 5/1973 | Higuchi et al. | 424/455 |
| 3,758,686 | 9/1973 | Sieger et al. | 424/241 |
| 3,881,026 | 4/1975 | Shepherd et al. | 424/81 |
| 4,230,687 | 10/1980 | Sair et al. | 472/22 |
| 4,282,216 | 8/1981 | Rovee et al. | 424/240 |
| 4,321,117 | 3/1982 | Kaetsu et al. | 204/159 |
| 4,435,524 | 3/1984 | Dinbergs | 521/65 |
| 4,477,467 | 10/1984 | Nishizawa et al. | 424/317 |
| 4,478,818 | 10/1984 | Shell et al. | 424/16 |
| 4,525,340 | 6/1985 | Lange et al. | 424/16 |
| 4,542,069 | 9/1985 | Mauz et al. | 428/402 |
| 4,548,990 | 10/1985 | Mueller et al. | 526/332 |
| 4,551,332 | 11/1985 | Stillman | 424/195 |
| 4,590,068 | 5/1986 | Berthet et al. | 424/81 |
| 4,690,825 | 9/1987 | Won | 424/501 |
| 4,734,286 | 3/1988 | Mahieu et al. | 525/154 |

FOREIGN PATENT DOCUMENTS

| | | |
|---|---|---|
| 2692M | 7/1964 | France . |
| 3407024 | 9/1985 | Germany . |
| 60-97915 | 5/1985 | Japan . |
| 1239965 | 3/1969 | United Kingdom . |
| 2156676 | 10/1985 | United Kingdom . |

OTHER PUBLICATIONS

*Physicans' Desk Reference* (PDR), 38th ed., Medical Economics Co., Inc. Oradell, NJ, pp. 1437–1438 (1984).

*Primary Examiner*—Edward J. Webman
*Attorney, Agent, or Firm*—Heller Ehrman White & McAuliffe

[57] ABSTRACT

Retinoic acid compositions intended for topical application are incorporated in novel formulations in which they are retained as impregnants inside the pores of porous solid particles or microspheres. The pores form a continuous network open to the exterior of the particles, permitting outward diffusion of the retinoic acid impregnant at a controlled rate depending on the pore size. The impregnated particles are prepared by impregnation of preformed particles with the retinoic acid.

20 Claims, 3 Drawing Sheets

000
METHODS AND COMPOSITIONS FOR TOPICAL DELIVERY OF RETINOIC ACID

This is a Continuation of application Ser. No. 07/802,664 filed Dec. 5, 1991, now abandoned which is a continuation-in-part of application Ser. No. 07/644,869, filed Jan. 23, 1991, now U.S. Pat. No. 5,145,675 which was a continuation of application Ser. No. 07/334,051, filed Apr. 5, 1989, now abandoned which was a division of application Ser. No. 07/091,641, filed Aug. 31, 1987, now abandoned which was a continuation-in-part of application Ser. No. 06/810,478, filed Dec. 18, 1985; now abandoned; Ser. No. 06/846,321, filed Mar. 31, 1986; now abandoned; Ser. No. 06/896,956, filed Aug. 15, 1986 now abandoned; Ser. No. 06/925,081, filed Oct. 30, 1986 now abanoned; Ser. No. 06/925,082, filed Oct. 30, 1986 now abandoned; Ser. No. 06/932,613, filed Nov. 11, 1986 now abandoned; Ser. No. 06/933,243, filed Nov. 21, 1986 now abandoned; Ser. No. 06/936,520, filed Dec. 1, 1986 now abandoned; and Ser. No. 06/940,754, filed Dec. 10, 1986 now abandoned. The full disclosures of each of these references are incorporated herein by reference.

BACKGROUND OF THE INVENTION

The present invention relates to controlled release compositions comprised of porous polymeric microbead carriers retaining vitamins within their pores. The invention further relates to methods of preparing such compositions and their methods of use.

Vitamins are chemically unrelated, fairly complex organic substances that are essential in small amounts for the maintenance of normal metabolic functions. Vitamins are not synthesized within the human body and must therefore be furnished from exogenous sources. Natural sources of vitamins include plant and animal tissue.

Vitamins can be broadly categorized as either fat-soluble or water-soluble. Vitamins A, D, E and K are fat soluble and are absorbed in association with lipids. Vitamins $B_1$, $B_2$, $B_5$, $B_{12}$, $B_{15}$, $B_{17}$, C, niacin, folic acid, pantothenic acid, biotin, bioflavonoids, choline, inositol and F are examples of water-soluble vitamins.

Vitamins A, D and E, and derivatives thereof, including esters such as vitamin A palmitate, vitamin E acetate and vitamin E palmitate and substances which contain such vitamins and vitamin derivatives, such as fish oils, have long been known to be useful for various topical therapeutic and cosmetic purposes. Creams, ointments and powders containing vitamins A and D as such or in cod liver oil have been used for the prevention and treatment of prickly heat and diaper rash in infants. Vitamin E and vitamin E esters, such as the acetate and palmitate, have been used, typically in creams, ointments, lotions, oils and other cosmetic formulations, as skin moisturizers and smoothers, to treat chronic skin diseases, to aid in healing burns and wounds, to reduce scarring from wounds, as topical anti-inflammatory agents, and to protect the skin from damage from ultraviolet rays.

Vitamin-containing therapeutic and cosmetic creams, ointments, lotions, oils and like formulations feel greasy or oily when applied, and often leave residues which are difficult to remove from the skin. Vitamin-containing powder preparations enable only limited amounts of vitamin to penetrate the skin.

Vitamins are also used as additives in preparations primarily intended for purely cosmetic use, such as lip balms, lipsticks, blushers, eyeshadows and foundations.

Retinoids are a group of compounds consisting of vitamin A and its analogs. In addition to their effectiveness in enhancing vision and fertility, the compounds in this group are effective as keratolytic agents, and as such are used topically to retard and ameliorate photoaging of facial skin and senile keratosis, to treat acne vulgaris, and to treat warts.

Vitamin A itself is a term used to designate several biologically active compounds, principally the alcohols retinol, whose chemical name is 3,7-dimethyl-9-(2,6,6-trimethyl-1-cyclohexen-1-yl)-2,4,6,8-nonatetrae-nol, and 3-dehydroretinol. Other retinoids include the corresponding acids, aldehydes, esters and aromatic derivatives of these. The most common of the acids is retinoic acid, or 3,7-dimethyl-9-(2,6,6-trimethyl-1-cyclohexen-1-yl)-2,4,6,8-nonatetraenoic acid. The all-trans-form, of retinoic acid is also known by the common name tretinoin. Other acids within the class include the 9,10-cis-form and the 13-cis-form. Examples of esters are the methyl ester and the ethyl ester. The acids are crystalline under ambient conditions, soluble in fats and alcohols. The esters are liquids under ambient conditions. The acids and their derivatives are of particular interest for their high therapeutic value.

For topical application, retinoids are typically formulated as creams, ointments, oils and the like. In such formulations, however, retinoids rapidly degrade and lose activity. In addition, moderate to severe skin irritation frequently results from the use of these formulations. Still further, these formulations usually feel oily or greasy when applied, and tend to leave residues on the skin which are difficult to remove.

SUMMARY OF THE INVENTION

A novel formulation for topically delivering retinoic acid and therapeutically effective salts thereof has now been developed with significant advantages over preexisting formulations. In accordance with the present invention, porous particles of an inert solid material contain retinoic acid and derivatives thereof, alone or in solution, retained inside the pores of the particles by capillary forces. The pores are interconnected and open to the particle surface, permitting full diffusion outward of the retained retinoic acid under particular conditions. The particles, which are preferably and most conveniently in the form of microspheres, are used either alone as a powder or as a dispersion in a suitable vehicle in a form resembling those of conventional skin preparations such as liniments, gels, lotions or ointments.

More specifically, the delivery systems of this invention constitute pre-formed, discrete, minute, high-capacity, hydrophobic, macroporous or macroreticular cross-linked, monionogenic polymer beads into whose macropores there have been incorporated retinoic acid, derivatives thereof, and optionally other active or inert substances, in solid form or dissolved in a suitable organic solvent, alone or together with other formulating materials.

In the case of retinoids, porous particles of an inert solid material contain one or more retinoids, alone or in solution, retained inside the pores of the particles by the pore structure if solid and by capillary forces if liquid. The pores are interconnected and open to the particle surface, permitting full diffusion outward of the retained retinoids. The particles, which are preferably and most conveniently in the form of microspheres, are used either alone as a powder or as a dispersion in a suitable vehicle in a form resembling those of conventional skin preparations such as lini-ments, gels, lotions or ointments.

In general, retinoids diffuse out of the pores into either the vehicle if one is used or the natural bodily secretions (sebum) present on one's skin at the applied area, in accordance with known principles of the diffusion of one substance through another.

The particles function as controlled delivery systems for the retinoids, providing a wide range of advantages over the conventional formulations. Release of the vitamins from the pores of the beads occurs in sustained manner, providing a continuous fresh supply of retinoids to the epidermal area to which the preparation has been applied. Until it is released, the retinoid is essentially unexposed to the atmosphere, and hence contact with oxygen and the risks of oxidation and decomposition are minimal. The formulation remains stable and active for a longer period of time, enhancing its shelf life. In addition, the particles have a dry, smooth, comfortable feel to the skin.

The activity-time curve of the vitamin is thus extended and flattened out. The magnitude of the release rate is controlled by the pore volume distribution in the microsphere itself, notably the total pore volume and the average pore diameter. Selection of the values of these parameters according to predetermined standards provides control of the release rate to desired levels. This controlled release rate enhances the continuing treatment of the epidermal area, as sebum is continually produced by the skin. This also reduces the number of times that the skin formulation must be reapplied to the affected area.

The preparations remain active for a longer period of time after having been applied to the skin than conventional formulations, due to the sustained release character. The rate of release can be accelerated at any time thereafter by manual friction to stimulate the outward diffusion of the retinoic acid. Thus, deeply retained materials may be brought to the surface and made available for their activity at will, many hours after the application of the formulation, without the need for a repeat application.

A further advantage is the ability of the formulation to withstand a higher concentration of retinoids both inside the pores themselves and in the total preparation without the magnitude of side effects, particularly iritation, previously experienced at these levels. Surprisingly, it has been found that incorporation of retinoic acid into the polymeric carriers of the present invention can enhance efficacy when compared to topical application of the same amount of non-entrapped retinoic acid.

DETAILED DESCRIPTION OF THE INVENTION AND PREFERRED EMBODIMENTS

The beads or microspheres used in connection with the present invention are rigid, open-pore, chemically and biologically inert particles with the impregnant held inside the pores by capillary forces. The pores are interconnected and open to the particle surface to an extent that substantially full communication is provided between the internal pore space and the exterior of the particle.

In their most convenient form, the particles are generally spherical in shape, due to the use of suspension polymerization as a preferred method of preparation. While the microspheres may vary widely in size, those falling within the range of about one to about 100 microns in diameter, preferably from about 10 to about 40 microns, will provide the best results. Microspheres within these size ranges are appealing from an aesthetic point of view by imparting a smooth feel to the touch.

The pore dimensions within the spheres may also vary widely, with optimum dimensions depending on the chemical characteristics of the polymers used as well as the diffusive characteristics of the impregnant. Different systems will thus call for different optimum ranges of pore volume distribution to obtain the most desirable properties for the overall formulation. In general, however, best results are obtained with total pore volumes ranging from about 0.01 to about 4.0 cc/g, preferably from about 0.1 to about 2.0; surface areas ranging from about 1 to about 500 $m^2/g$, preferably from about 20 to about 200; and average pore diameters ranging from about 0.001 to about 3.0 micron, preferably from about 0.003 to about 1.0 micron. Following conventional methods of measuring and expressing pore sizes, the pore diameters are calculated from the measurement of the surface area by B.E.T. nitrogen multipoint analysis and from the measurement of the pore volumes by the mercury intrusion method. The calculation is one commonly done by those skilled in the art.

The microspheres are conveniently formed by suspension polymerization in a liquid-liquid system. In general, a solution containing monomers, a polymerization catalyst (if used), and an inert but fully miscible liquid is formed which is immiscible with water. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting rigid beads are recovered from the suspension. The beads at this point are solid porous structures, the polymer having formed around the inert, water-immiscible liquid, thereby forming the pore network. The liquid has accordingly served as a porogen, or pore-forming agent, and occupies the pores of the formed beads.

Suitable porogens will be liquids meeting the following criteria:

1. They are either fully miscible with the monomer mixture or capable of being made fully miscible by the addition of a minor amount of non-water-miscible solvent;

2. They are immiscible with water, or at most only slightly soluble;

3. They are inert with respect to the monomers, and stable when in contact with any polymerization catalyst used and when subjected to any conditions needed to induce polymerization (such as temperature and radiation); and 4. They are normally liquids or have melting points below the polymerization temperature. Solids can frequently be converted to liquid form by being dissolved in a solvent or by forming eutectic mixtures.

When using this method, the steps must be performed under an inert atmosphere such as nitrogen. If a polymerization catalyst is used, it must be one which does not oxidize the impregnant, if the latter is susceptible to oxidation. Azo catalysts are examples of such catalysts. Also, polymerization temperatures are best held within a moderate range.

The retinoid impregnant may be placed inside the pores of preformed dry porous polymer beads. The product is thus prepared in two steps performed in sequence, the polymerization being performed first with a substitute porogen which is then removed and replaced by the retinoic acid present in a suitable solvent, typically acetone or isopropyl alcohol.

Preferred porogens include hydrocarbons, particularly inert, nonpolar organic solvents. Some of the most convenient examples are alkanes, cycloalkanes, and aromatics. Examples of such solvents are alkanes of 5 to 12 carbon atoms, straight or branched chain, cycloalkanes of 5 to 8 carbon atoms, benzene, and alkyl-substituted benzenes such as toluene and the xylenes. Removal of the porogen may then be effected by solvent extraction, evaporation, or similar conventional operations.

A further advantage of the use of this two-step process is that it permits the removal of unwanted species from the polymerized structures prior to incorporation of the impregnant. Examples of unwanted species include unreacted monomers, residual catalyst, and surface active agents and/or dispersants remaining on the sphere surfaces. A further advantage of this technique is that it permits one to select the amount and type of porogen as a means of controlling the pore characteristics of the finished bead. One is thus no longer bound by the limitations of the impregnant as it affects the structure of the bead itself. This permits partial rather than full filling of the pores with the retinoid, and further control over pore size and distribution by selection among swelling and non-swelling porogens.

Extraction of the porogen and its replacement with (i.e., impregnation of the dry bead with) the retinoid in the two-step procedure may be effected in a variety of ways, depending on the chemical nature of the porogen and its behavior in combination with that of the other species present. The beads are first recovered from the suspension by filtration, preferably using vacuum filtration apparatus (such as a Buchner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used—i.e., where the porogen, unreacted monomer and water will form an azeotrope. In these cases, steam distillation is an effective way of extracting porogen from the beads. This again may be followed by drying under vacuum.

Once the beads are rendered dry and free of the substitute porogen and any unwanted organic materials, they are impregnated with the retinoid impregnant according to conventional techniques. The most convenient such technique is contact absorption. The retinoid is first dissolved in a solvent, and the resulting solution is absorbed by the beads. The solvent may either be retained in the finished product or removed by conventional means such as evaporation or extraction using a further solvent. Since retinoic acid has limited solubility in most solvents, high contents in the finished bead can be attained by repeated absorptions each followed by solvent removal.

The polymerization process and the various parameters and process conditions involved in the polymerization can be selected and adjusted as a means of controlling the pore characteristics and consequently the capacity and release characteristics of the ultimate product. For example, proper selection of the cross-linking means, the amount and type of cross-linking agent, and the amount and type of porogen are means of attaining such control. Certain polymerization conditions may also be varied to such effect, including temperature, degree of radiation where used, degree of agitation and any other factors affecting the rate of the polymerization reaction.

Cross-linking in the polymer formation is a major means of pore size control. Monomers which may be polymerized to produce cross-linked polymer beads in accordance with the present invention include polyethylenically unsaturated monomers, i.e., those having at least two sites of unsaturation, and monoethylenically unsaturated monomers in combination with one or more polyethylenically unsaturated monomers. In the latter case, the percentage of cross-linking may be controlled by balancing the relative amounts of monoethylenically unsaturated monomer and polyethylenically unsaturated monomer. The polymer beads of the present invention will have greater than 10% cross-linking, preferably from about 10% to about 80% cross-linking, and most preferably from about 20% to about 60% cross-linking. The percentage cross-linking is defined among those skilled in the art as the weight of polyethylenically unsaturated monomer or monomers divided by the total weight of monomer, including both polyethylenically unsaturated and monoethylenically unsaturated monomers.

Monoethylenically unsaturated monomers suitable for preparing polymer beads for the polymer delivery system include ethylene, propylene, isobutylene, diisobutylene, styrene, ethylvinylbenzene, vinylpyridine, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isopropene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetri-methacrylate, divinylsulfone; polyvinyl and polyallyl ethers of ethylene glycol, of glycerol, of pentaerythritol, of diethyleneglycol, of monothio- and dithio-derivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

The preferred polymer bead of the present invention will be free from reactive groups which will interact with the porogen and the active ingredient which is ultimately incorporated in the composition. In particular, the beads should be free from reactive amino, hydroxyl, carboxylic, and other reactive functionalities. Such beads will not readily undergo unwanted reactions, will be stable over a wide pH range, will resist moderate oxidation and reduction, will be stable at higher temperatures, will resist attack by moisture, and will have a relatively long shelf life.

Particularly preferred polymer delivery systems of the present invention are formed by the copolymerization of styrene and divinylbenzene, vinyl stearate and divinylbenzene, 4-vinylpyridine and ethylene glycol dimethacrylate, or methylmethacrylate and ethylene glycol dimethacrylate. Usually, the monoethylenically unsaturated monomer will be present at from about 20% to 80% of the monomer mixture, with the polyethylenically unsaturated monomer forming the remainder of the mixture. Particularly preferred is the styrene-divinylbenzene polymeric bead which consists essentially of a hydrocarbon backbone with benzene rings and which is substantially completely free from reactive groups.

Once the microspheres are formed and dried, they are impregnated with the impregnant by contact absorption. In particular, the retinoid impregnant will be used in the form of a solution in a suitable organic solvent for purposes of decreasing viscosity and facilitating absorption. Examples of such solvents are liquid petrolatum, ether, petroleum ether, alcohols including methanol, ethanol and higher alcohols, aromatics including benzene and toluene, alkanes including pentane, hexane and heptane, ketones including acetone and methyl ethyl ketone, chlorinated hydrocarbons including chloroform, carbon tetrachloride, methylene chloride and ethylene dichloride, acetates including ethyl acetate, and oils including isopropyl myristate, diisopropyl adipate and mineral oil. Preferred are acetone and isopropanol, where solutions of up to about 1% by weight retinoic acid can be obtained.

After absorption of the solution, the solvent can be evaporated or, if desired, retained inside the pores together with the impregnant. Usually, the absorption/evaporation cycle will be reported at least once, usually twice, and frequently three or more times, in order to obtain final concentrations of 1%, or higher.

Other formulating materials, such as carriers or adjuvants such as fragrances, preservatives, antioxidants, and other emollients can also be present, and will be incorporated into and onto the beads together with the impregnants and any other materials present.

The retinoid impregnant, whether it be pure (solid) active ingredient, a mixture of active ingredients or a solution of active ingredient, will generally comprise between approximately 1% and approximately 20% of the total weight of the impregnated beads, usually being from about 1% to 2.5% of the total weight.

The retinoid impregnated beads of the present invention will be used for topical treatment of damaged skin, where the damage can result from sun exposure, acne, chronological aging, or the like. The impregnated beads may be used alone or more commonly in the form of fluid compositions or preparations similar to those commonly used for skin treatment, for example: gels, creams, lotions, ointments, sprays, powders, or oils. Appropriate vehicles for particular areas or methods of application will be readily apparent to those skilled in the art. When liquid vehicles are used (such as gels, creams, lotions, ointments or oils) and the impregnant is a solution of an active ingredient in a solvent, the solvent and vehicle must be immiscible so that outward diffusion of the active ingredient will not be accelerated by mutual diffusion between the solvent and vehicle. Appropriate combinations will therefore include the combination of a polar solvent and a nonpolar vehicle, and the combination of a nonpolar solvent and a polar vehicle.

The following examples relate to the preparation and utility of the vitamin compositions of the present invention. The examples are offered solely for purposes of illustration, and are intended neither to limit nor define the invention in any manner. All parts and percentages are by weight, unless otherwise stated.

EXPERIMENTAL

EXAMPLE ONE

A 2000 ml four-necked reaction flask equipped with a motorized stirrer, reflux condenser, thermometer, and nitrogen inlet was evacuated and purged with nitrogen. 800 parts of deionized water, 6.4 parts of gum arabic and 6.4 parts of a sodium-based lignosulfonate available from Reed Lignins, Inc., under the trademark Marasperse N–22, were charged to the reaction flask. The mixture was heated, with stirring, in an oil bath at about 50° C. until the dispersants (gum arabic and lignosulfate) dissolved to form an aqueous phase.

To this mixture was then added a freshly prepared solution of 90.5 parts of styrene (99.8% purity), 55 parts of commercial divinylbenzene (55.6% divinyl benzene, 42.3% ethylvinylbenzene), 2 parts benzoyl peroxide (70% active ingredient and 30% water), and 69.4 parts of heptane (porogen). The aqueous phase and organic solution were agitated by stirring at a rate adjusted to give a plurality of droplets having an average droplet diameter of about 10–60 microns, as determined by visual observation of a sample of the droplets with an optical microscope (400×) with the droplets being stabilized by the dispersants. This rate was approximately 1200 rpm. The reaction mixture was then heated to about 80° C. and maintained at that temperature for about 12 hours, at the previously adjusted stirring rate, to form porous beads of cross-linked styrene/divinylbenzene copolymer having toluene entrapped within the network of pores. The mixture was then cooled and the porous polymeric beads are removed from the reaction flask by filtration. The filtered beads were washed initially three times with one liter portions of deionized water to remove the dispersants, followed by three washes with 0.6 liter portions of isopropanol to remove any residual, unreacted monomer and the toluene used as the porogen during polymerization. The beads were then dried in an oven at 80° C. for eight hours.

The average particle diameter of these beads, which are white and opaque in appearance, indicating their macroporosity, was less than 35 microns, as measured by a mercury intrusion porosimeter or by optical microscopy.

The calculated or theoretical cross-linking density of the purified beads was 21.01%. This density was calculated by multiplying the weight of divinylbenzene (55 parts) by the purity of the divinylbenzene (0.556) to get the actual weight of pure divinylbenzene which was then divided by the total weight of monomer (90.5 parts+55 parts) and multiplied by 100.

The surface area of a sample of the purified beads was determined by the B.E.T. method to be 36.41 meters$^2$/gram while the pore volume was determined by nitrogen adsorption isotherm to be 0.206 ml/gram. The B.E.T. method is described in detail in Brunauer, S. Emmet, P. H., and Teller, E., J. Am. Chem. Soc., 60, 309-16 (1938). The nitrogen adsorption isotherm method is described in detail in Barrett, E. P., Joyner, L. G. and Helenda, P. P., J. Am. Chem. Soc., 73, 373–80 (1951).

EXAMPLE TWO

The procedure of Example One was repeated in every essential detail, except for the following: 800 parts of deionized water were used to dissolve 5.6 parts of gum arabic and 5.6 parts of Marasperse N-22 at about 23° C.; 105 parts of styrene and 95 parts of divinylbenzene were used; 2.8 parts of benzoyl peroxide (70% active ingredient and 30% water) and 120 parts of heptane were employed during polymerization and stirring was adjusted to give an average droplet diameter of below about 50 microns (rate approximately 800–1600 rpm); three 300 ml portions of isopropanol were used to wash the beads. The macroporous cross-linked polymer beads obtained had the following characteristics:

Calculated Cross-linking Density, %: 26.4
Average Particle Diameter, $\mu$: 25
Surface Area, m$^2$/g: 85.9
Pore Volume, ml/g: 0.44

EXAMPLE THREE

A two liter four-necked reaction flask equipped as described in Example One was evacuated and purged with nitrogen. An aqueous phase made up of 600 parts of deionized water, 6.0 parts of gum arabic and 6.0 parts of Marasperse N-22 was added to the flask, and an organic solution made up of 72.0 parts of methyl methacrylate, 78.0 parts of ethylene glycol dimethacrylate, 2.0 parts of benzoyl peroxide (70% active ingredient and 30% water) and 108.4 parts of toluene was dispersed in the aqueous phase with strong agitation (stirrer speed approximately 1000 rpm) to obtain a plurality of droplets having an average droplet diameter of below about 50 microns, as determined by visual observation of a sample of the droplets with an optical microscope (400x), with the droplets being stabilized by the dispersants.

The reaction mixture was then heated to 80° C. and maintained at that temperature for 12 hours while maintaining a nitrogen flow of 6 ml/minute, to form porous beads of cross-linked methyl methacrylate/ethylene glycol dimethacrylate copolymer having toluene entrapped within the pores. The reaction mixture was then cooled and the beads were collected by filtration, washed three times with 1000 part portions of water, then three times with 1000 part portions of isopropanol, and then dried at 80° C. for about 8 hours.

The calculated or theoretical cross-linking density of the purified beads was 52%, and was calculated by dividing the weight of ethylene glycol dimethacrylate (78.0 parts) by the total weight of monomer (72.0 parts+78.0 parts) and then multiplying by 100.

The surface area of a sample of the purified beads is 96 meters$^2$/gram and the pore volume is 0.36 ml/gram, determined as described in Example One above.

EXAMPLE FOUR

The procedure of Example Three was again repeated in every essential detail except for the following: 400 parts of deionized water were used to dissolve 4.0 parts of gum arabic and 4.0 parts of Marasperse N-22; 70 parts of methyl methacrylate and 30 parts of ethylene glycol dimethacrylate were used; 1.0 part of lauroyl peroxide and 69.4 parts of toluene were employed during polymerization; the reaction was conducted at 85° C. for 12 hours. The resulting polymer beads were collected and washed with three 1000 ml portions of deionized water followed by three 1000 ml portions of isopropanol, and then dried at 80° C. for about 8 hours. The macroporous cross-linked polymer beads obtained had the following characteristics:

Calculated Cross-linking Density, %: 30
Average Particle Diamter, $\mu$m: 30
Surface Area, M$^2$/g: 12.54
Pore Volume, ml/g: 0.170

EXAMPLES FIVE-SEVEN

By repeating the procedure of Example Four in every essential detail except for the weights of monomers and solvents employed, the macroporous cross-linked polymer beads described in Table 1 below were obtained.

TABLE 1

| Example | Methyl methacrylate, g | Ethylene Glycol Dimethacrylate, g | Porogen Toluene, g | Calculated Cross-linking Density, % | Average Particle Diameter, $\mu$m | Surface Area m$^2$/g | Pore Volume, ml/g |
|---|---|---|---|---|---|---|---|
| 5 | 20.0 | 80.0 | 85.6 | 80.0 | 30 | 301.93 | 0.553 |
| 6 | 40.0 | 60.0 | 69.4 | 60.0 | 25 | 95.07 | 0.368 |
| 7 | 80.0 | 20.0 | 86.7 | 20.0 | 40 | 0.72 | 0.044 |

EXAMPLE EIGHT

A 70 part portion of the macroporous cross-linked polymer beads prepared as described in Example Three above was mixed at room temperature with 157 parts of isopropanol in a glass beaker with an agitator. 30 parts of vitamin E linoleate are added slowly, with stirring, and the resulting suspension is stirred for about five minutes. The solvent is then allowed to evaporate to dryness in a fume hood at room temperature for 2 days. The beads contain 30.0% vitamin E linoleate entrapped within their macropores.

EXAMPLE NINE

By repeating the procedure of Example Eight using 35 parts of the styrene divinylbenzene macroporous cross-linked polymer beads prepared as described in Example Two, 15 parts of vitamin E linoleate and 86.7 parts of isopropanol as the solvent, beads containing 30% vitamin E linoleate entrapped within their macropores are obtained.

EXAMPLE TEN

By again repeating the procedure of Example Eight using 350 parts of the methyl methacrylate/ethylene glycol dimethacrylate macroporous cross-linked polymer beads prepared as described in Example Three, 160 parts of vitamin E linoleate and 200 parts of isopropanol, beads containing 31% vitamin E linoleate entrapped within their macropores are obtained.

EXAMPLES ELEVEN-SIXTEEN

The procedure of Example Eight is repeated using the following vitamins, vitamin derivatives, vitamin-containing substances and solvents in the indicated amounts indicated in Table 2.

TABLE 2

| Active Ingredient, parts | | Macroporous Polymer parts | Solvent, parts | |
|---|---|---|---|---|
| Vitamin A, | 1.0 | 1.0 | Ethanol, | 4.0 |
| Vitamin D, | 30.0 | 30.0 | Isopropanol, | 39.0 |
| Vitamin E, | 30.0 | 30.0 | Isopropanol, | 39.0 |
| Vitamin E, Acetate, | 15.0 | 35.0 | Ethanol, | 78.5 |
| Vitamin E, Palmitate | 15.0 | 35.0 | Ethanol, | 78.5 |
| Cod Liver Oil, | 40.0 | 40.0 | Isopropanol, | 125.6 |

In each case, methyl methacrylate/ethylene glycol dimethacrylate macroporous cross-linked polymer beads containing the respective active ingredients in the following percentages (Table 3) are obtained.

TABLE 3

| Active Ingredient | % |
|---|---|
| Vitamin A | 50 |
| Vitamin D | 50 |
| Vitamin E | 50 |
| Vitamin E acetate | 30 |
| Vitamin E palmitate | 30 |
| Cod liver oil | 50 |

EXAMPLE SEVENTEEN

Three 0.4 gram portions of each of:
1. commercially available night cream;
2. the same commercially available night cream admixed with 1% vitamin E linoleate; and
3. the same commercially available night cream admixed with 1% polymer beads containing entrapped vitamin E linoleate (entrapped vitamin E linoleate equals 32% of the weight of beads), are rubbed onto three separate areas on a volunteer's lower arm. The viscoelastic properties of the treated skin of the arm were measured over a five minute period with an electrodynamometer. The technique is described in detail in M. S. Christensen, C. W. Hargens III, S. Nacht, and E. H. Gans, J. Invest. Dermatol, 69:282 (1977).

The three areas are rubbed, applying equal pressure to each, after 15 and 24 hours. The results of the tests, in terms of percent increase in skin softening and release upon demand of the substances tested are measured.

The first compound is the commercially available night cream. It exhibits between a 25% and 30% increase in skin softening about one hour after application, increasing to about 40% skin softening approximately five hours after the initial application. Over the next 10 hours, its effectiveness rapidly declines to a 0% increase in skin softening. Rubbing the area to which the night cream was applied 15 hours after application has no effect.

The second compound is the night cream with admixed 1% vitamin E linoleate. It exhibits about a 40% increase in skin softening one hour after application, increasing to around 44% at five hours after application. It then drops to about a 15% increase over the next 10 hour period. Fifteen hours after application, the affected area is rubbed, causing the % increase in skin softening to remain level at 15% for nearly an hour before dropping to zero an hour later.

The third compound is the night cream with admixed 1% polymer beads that contain vitamin E linoleate, where the entrapped vitamin E linoleate is 32% of the weight of the beads. One hour after application, this compound exhibits between a 30% and 35% increase in skin softening. This increases to approximately 44% at the five hour mark. Over the next ten hours, this value declines to zero. By rubbing the skin area fifteen hours after the initial application, the increase in skin softening rapidly increases to between 20 and 25% over the next hour before declining to zero. Thus, a release of the active ingredient from the polymer beads can be effected at will be simply rubbing the area to which the beads were applied, even many hours after the initial application.

EXAMPLE EIGHTEEN

A 99-part portion of the macroporous cross-linked polymer beads prepared in Example Two above is mixed at room temperature with 1 part of retinoic acid (all-trans-form) dissolved in 50 parts of acetone. The resulting suspension is hand-stirred for a few minutes, and the solvent is then allowed to evaporate to dryness in a fume hood at room temperature. The beads are calculated to contain 1% of retinoic acid retained within the pores.

EXAMPLE NINTEEN

A 180-part portion of the macroporous cross-linked polymer beads prepared in each of Examples One through Seven is mixed at room temperature with 214 parts of retinoic acid (all-trans-form) dissolved in a solution of 57.6 parts of (Migiol 840, an emolument to enhance the solubility of retinoic acid,) and 120 parts of acetone. The resulting suspension is handstirred and the solvent is then allowed to evaporate. The beads are calculated to contain 1.0% of retinoic acid and 24% of isopropyl myristate retained within the pores.

EXAMPLE TWENTY

Figure 1:
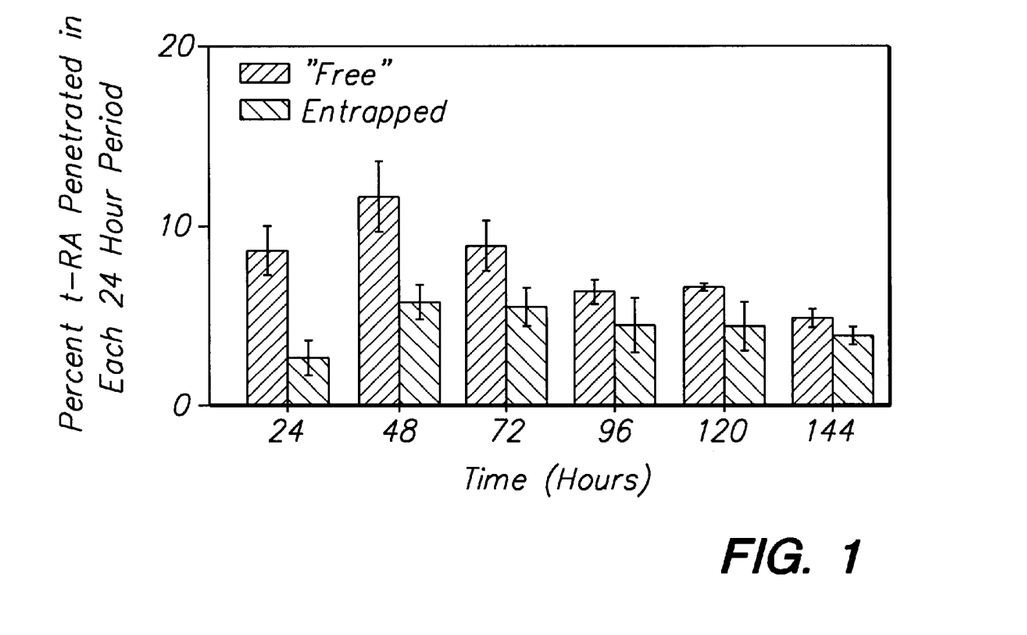
FIG. 1 is a chart which compares skin penetration of trans-retinoic acid released from the polymer bead delivery system of the present invention with free trans-retinoic acid, where both are present in a gel.

Trans-retinoic acid was entrapped in macroporous cross-linked polymer beads (1% by weight retinoic acid) prepared as in Example Nineteen, and the beads were formulated into an appropriate gel. Skin permeability studies were performed on hairless mouse skin with formulations containing retinoic acid (at 0.1% concentration) in gels containing either the free retinoic acid or the bead-entrapped retinoic acid. FIG. 1 shows the percentage of skin penetration measured over six successive 24-hour periods. The formulation containing the free retinoic acid delivered a large amount of drug through the skin in the first 48 to 72 hours, while the bead-entrapped formulation delivered the retinoic acid at a much slower and constant rate (after an initial lag).

Figure 2:
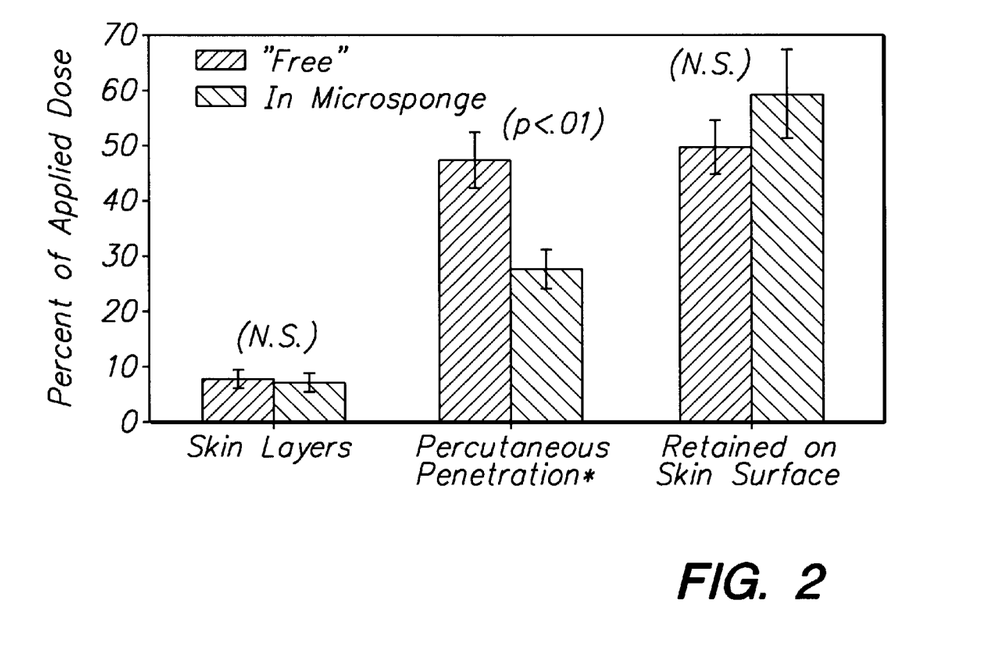
FIG. 2 is a chart which compares skin distribution of trans-retinoic acid after 144 hours.

At the end of the skin permeability study, when the distribution of the drug in the different compartments was evaluated, it was seen that the amount of drug which penetrated percutaneously from a bead-entrapped formulation was half of that which penetrated from the skin with the free drug formula. When the skin layers were evaluated for drug content, however, there was no significant difference (FIG. 2). This result indicates that the bead-entrapped delivery system of the present invention was able to reduce systemic absorption by a factor of two, but it did not interfere with the amount of retinoic acid taken up by the skin, the site of therapeutic action.

Figure 3:
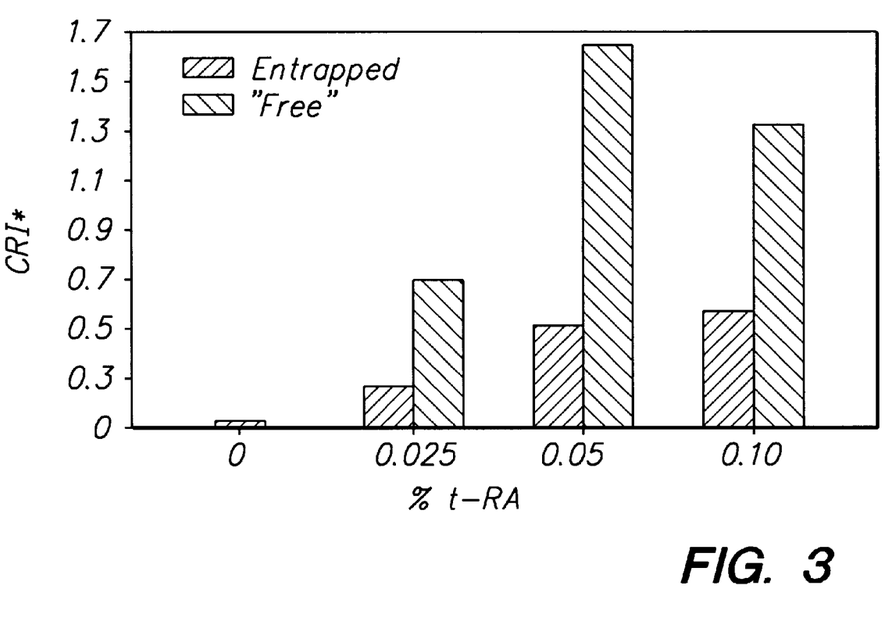
FIG. 3 is a chart which compares cumulative irritancy between entrapped and non-entrapped trans-retinoic acid formulations at different concentrations.

Based on these results, the bead-entrapped retinoic acid formulation should exhibit reduced irritancy in comparison with free retinoic acid. This result was confirmed in a 14-day cumulative irritancy study in humans in which both formulations were tested. The results, presented in FIG. 3, indicate that the formulation containing the entrapped drug was much less irritating than the formulation containing the free drug at anyone of the three concentrations tested.

In order to prove that efficacy of the retinoic acid was not impaired, a study on epidermal photo-damage repair in mice was conducted. In this test, hairless mice were exposed to UV radiation chronically for 10 weeks until a significant amount of photo-damage was induced in the epidermis. At this point, the UV exposure was discontinued and, after an appropriate rest period, the animals were treated with the experimental formulations for another 10 weeks to induce epidermal repair. Then the animals were sacrificed and the extent of repair was evaluated in histological sections of the exposed skin and measured as the depth of repair in microns. Table 4 presents the results of this study.

TABLE 4

| Formulation | Repair Depth (Microns) |
| --- | --- |
| 0.1% Retin ® A | 74.6 |
| 0.05% t-RA (entrapped) | 71.7 |
| 0.10% t-RA (entrapped) | 103.3 |
| 0.15% t-RA (entrapped) | 79.2 |
| Blank Beads (control) | 34.1 |

A commercial product (Retin-A®, Ortho Division, Johnson & Johnson Company) containing 0.1% trans-retinoic acid induced a significant repair of the photo-damage. Surprisingly it was found that formulations containing the same concentration of retinoic acid in beads induced a 50% better repair and that bead-entrapped formulations containing one-half of the retinoic acid concentration were similar in efficacy to the commercial product tested. When an even higher concentration of active ingredient in microsponges were tested (outside the accepted therapeutic range) then the repair was reduced, possibly due to the increased irritancy that was observed in these animals.

EXAMPLE TWENTY-ONE

Trans-retinoic acid was entrapped in macroporous cross-linked polymer beads (0.025% and 0.10% by weight) prepared as in Example Nineteen, and the beads were formulated in a cream base. Empty beads (containing no trans-retinoic acid) were also combined in a cream base as a control, and a blind study was performed comparing the efficacy of the two formulations and the control as follows.

One hundred sixty-five (165) subjects (male and female aged 15 to 35 years) were divided into three groups of 55. All subjects met the following criteria. At the time of selection, each subject had no less than 10 or more than 100 comedones (open and closed) and no less than 5 or more than 50 inflammatory lesions (papules and pustules). In addition to these, the subjects had moderate to extremely oily skin. On a global assessment scale of 0–8.0 (see scale definition below), subjects had a score of at least 0.5.

During the study, subjects refrained from use of medicated soaps or washes, facial cosmetics, creams, fresheners, and aftershave lotions. Subjects cleansed their face with a mild soap (Neutrogena or similar) without harsh rubbing each evening before retiring. After each of these cleansings, the assigned formulation was applied to the full face and neck, if necessary. Subjects did not cleanse their face for at least 3 hours after application of the medication.

The subjects were examined on day 0, and at weeks 2, 4, 8 and 12 for evidence of inflammation, peeling, and degree of oiliness/dryness. These observations were scored as follows:

Inflammation: Erythema is one of the parameters of inflammation—the others being swelling, pain and warmth. Under this method of evaluation, erythema is the most frequently observed sign. Edema is synonymous with swelling. Vesiculation and bullae have the same pathophysiological mechanism as edema but they are localized and of greater severity.

Inflammation was scored on the facial, eye and neck areas using the following scale: 0=no erythema 0.5=doubtful erythema 1=mild erythema 2=moderate erythema 3=marked erythema 4=erythema and edema 5=vesiculation 6=bullae, hemorrhage or ulceration (specify)

Patients with an initial generalized erythema score of 2 or greater were excluded from the study.

Peeling was scored on the facial, eye and neck areas using the following scale: 0=none 0.5=doubtful 1=slight 2=moderate 3=marked 4=severe Patients with an initial peeling score of 2 or greater were excluded from this study.

Oiliness/Dryness was scored on the facial, eye and neck areas using the following scale: −4=extremely oily −3=very oily −2=moderately oily −1=slightly oily +0=normal +1=slightly dry +2=moderately dry +3=quite dry (manifested by roughness and/flaking) +4=severe dryness with pronounced flaking At each examination, the number of each type of acne lesions was carefully counted and recorded. Thus, separate counts were obtained for open and closed comedones and for papules and pustules. In addition, a global assessment of the acne was made at each visit based on the visual acne scale designed by W. Cunliffe (The General Infirmary at Leeds, England). The acne condition of the patient was compared against sixteen control standard photographs and assigned a global numerical (0–8.0) value.

Figure 4:
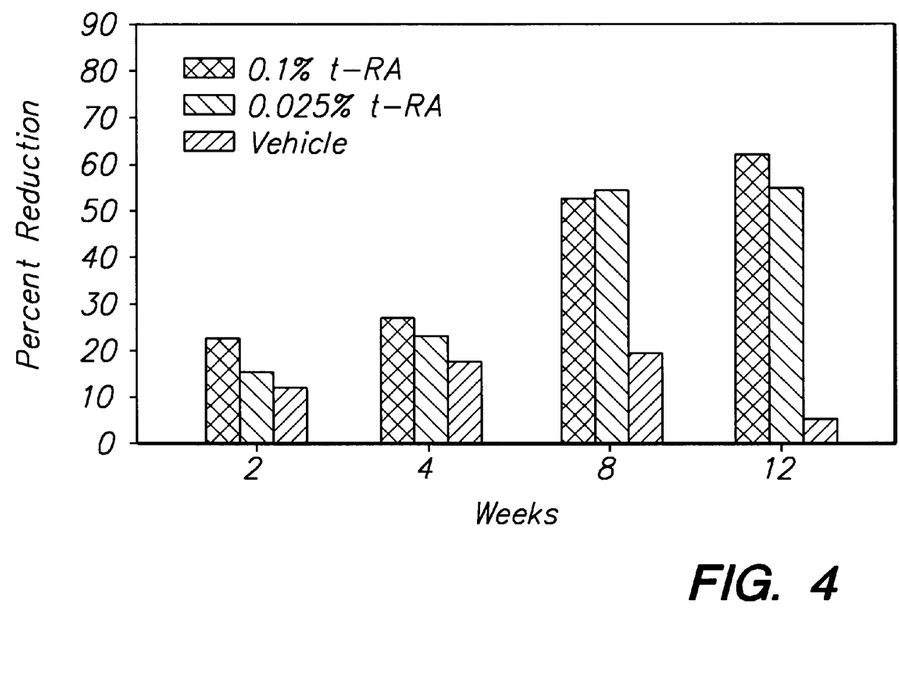
FIG. 4 is a chart which compares the percent reduction in the number of non-inflammatory acne lesions among different concentrations of the retinoic acid bead formulations of the present invention.
Figure 5:
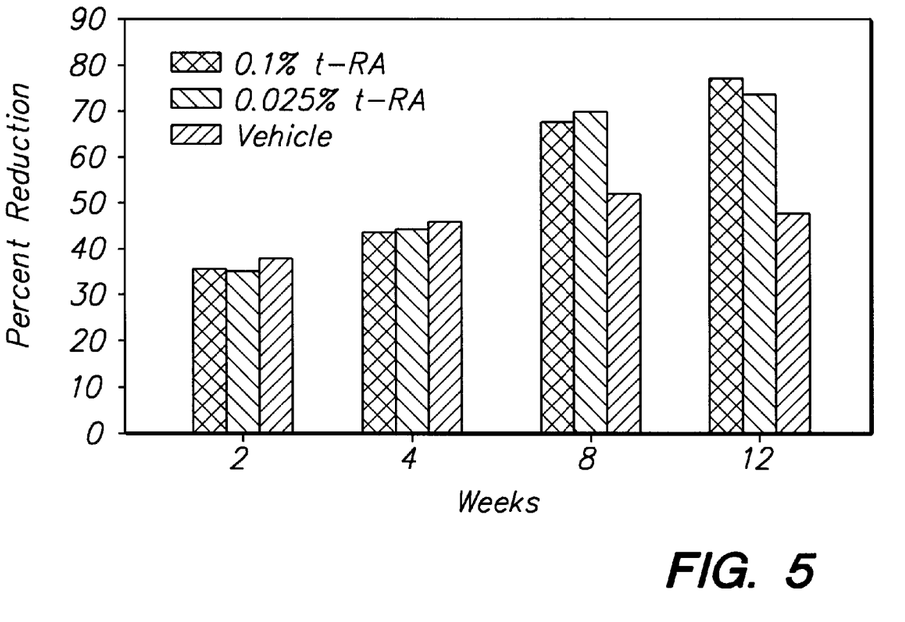
FIG. 5 is a chart which compares the percent reduction in the number of inflammatory lesions in the same study depicted in FIG. 4.
Figure 6:
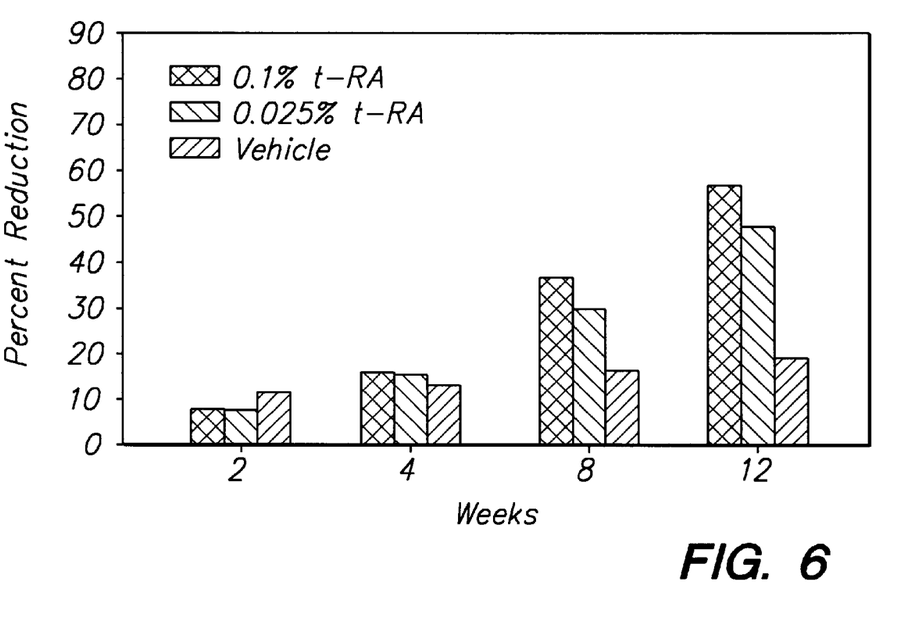
FIG. 6 is a chart which compares the global acne score in the same study depicted in FIGS. 4 and 5.

The results of this study are summarized in FIGS. 4–6. In FIG. 4, it can be seen that the percentage reduction in non-inflammatory lesions is substantially the same for the 0.1% and 0.025% formulations, particularly at the end of the study. In FIG. 5, the efficacy of the more and less concentrated formulations in treating inflammatory lesions is shown to be almost identical. Similar results are also seen in the global acne score of FIG. 6.

Thus, it can be seen that entrapment of the retinoic acid in the bead system of the present invention permits use of reduced concentrations of retinoic acid with substantially the same effectiveness.

In summary, it has been demonstrated that entrapping retinoic acid in the beads of the present invention reduce irritancy while preserving efficacy. In some cases, the retinoic acid beads of the present invention actually increase efficacy, probably by reducing the aggressiveness of the retinoic acid on the skin.

The foregoing description is directed primarily to preferred embodiments and practices of the present invention. It will be readily apparent to those skilled in the art that further changes and modifications in the actual implementation of the concepts described herein can be made without departing from the spirit and scope of the invention as defined by the following claims.

What is claimed is:

1. A topical composition for the delivery of retinoic acid to the skin, the composition comprising:
   (a) solid particles composed of a cross-linked copolymer of monoethylenically unsaturated monomers and polyethylenically unsaturated monomers free from reactive functionalities and having a cross-linking density from 20% to 80%, wherein said particles contain a continuous noncollapsible network of pores open to the exterior of said particles, are spherical in shape, and have an average diameter of about 1 micron to about 100 microns, a total pore volume of about 0.01 cc/g to about 4.0 cc/g, a surface area of about 1 $m^2/g$ to about 500 $m^2/g$, and an average pore diameter of about 0.001 micron to about 3.0 microns, and
   (b) an impregnant comprising retinoic acid retained inside said pores in an amount effective to promote skin repair, wherein retention of said retinoic acid inside said pores reduces irritancy of the composition when compared to application of the same amount of free retinoic acid without loss of skin repair promotion activity.

2. A topical composition in accordance with claim 1 in which said retinoic acid is retained inside said pores as a solid.

3. A topical composition in accordance with claim 1 in which said retinoic acid is retained inside said pores in a solvent selected from the group consisting of ethers, esters, alcohols, aromatics, and alkanes.

4. A topical composition in accordance with claim 1 in which said solid particles have an average diameter of about 10 microns to about 40 microns, a total pore volume of about 0.1 cc/g to about 2.0 cc/g, a surface area of about 20 $m^2/g$ to about 200 $m^2/g$, and an average pore diameter of about 0.003 micron to about 1.0 micron.

5. A topical composition in accordance with claim 1 in which said solid particles are composed of a cross-linked copolymer of styrene and divinylbenzene.

6. A topical composition in accordance with claim 1 in which said solid particles are composed of a cross-linked copolymer of methyl methacrylate and ethylene glycol dimethacrylate.

7. A topical composition in accordance with claim 1 in which said solid particles are composed of a cross-linked copolymer of 4-vinylpyridine and ethylene glycol dimethacrylate.

8. A topical composition in accordance with claim 1 in which said solid particles are combined with a vehicle to form a composition selected from the group consisting of liniments, gels, lotions, and ointments.

9. A topical composition in accordance with claim 1 in which said impregnant comprises about 1% to about 20% by weight of the total weight of said solid particles and said impregnant.

10. A topical composition in accordance with claim 9 in which said impregnant comprises about 1% to about 2.5 by weight of the total weight of said solid particles and said impregnant.

11. A method for applying retinoic acid to the skin, the method comprising applying to the skin a topical composition comprising:
   (a) solid particles composed of a cross-linked copolymer of monoethylenically unsaturated monomers and polyethylenically unsaturated monomers free from reactive functionalities and having a cross-linking density from 20% to 80%, wherein said particles contain a continuous noncollapsible network of pores open to the exterior of said particles, are spherical in shape and have an average diameter of about 1 micron to about 100 microns, a total pore volume of about 0.01 cc/g to about 4.0 cc/g, a surface area of about 1 $m^2/g$ to about 500 $m^2/g$, and an average pore diameter of about 0.001 micron to about 3.0 microns, and
   (b) an impregnant comprising retinoic acid retained inside said pores in an amount effective to promote skin repair, wherein retention of said retinoic acid inside said pores reduces irritancy of the composition when compared to application of the same amount of free retinoic acid without loss of skin repair promotion activity.

12. A method in accordance with claim 11 in which said retinoic acid is retained inside said pores as a solid.

13. A method in accordance with claim 11 in which said retinoic acid is retained inside said pores in a solvent selected from the group consisting of ethers, esters, alcohols, aromatics, and alkanes.

14. A method in accordance with claim 11 in which said solid particles have an average diameter of about 10 microns to about 40 microns a total pore volume of about 0.1 cc/g to about 2.0 cc/g, a surface area of about 20 $m^2/g$ to about 200 $m^2/g$, and an average pore diameter of about 0.003 micron to about 10 micron.

15. A method in accordance with claim 11 in which said solid particles are composed of a cross-linked copolymer of styrene and divinylbenzene.

16. A method in accordance with claim 11 in which said solid particles are composed of a cross-linked copolymer of methyl methacrylate and ethylene glycol dimethacrylate.

17. A method in accordance with claim 11 in which said solid particles are composed of a cross-linked copolymer of 4-vinylpyridine and ethylene glycol dimethacrylate.

18. A method in accordance with claim 11 in which said solid particles are combined with a vehicle to form a composition selected from the group consisting of liniments, gels, lotions, and ointments.

19. A method in accordance with claim 11 in which said impregnant comprises about 1% to about 20% by weight of the total weight of said solid particles and said impregnant.

20. A method in accordance with claim 19 in which said impregnant comprises about 1% to about 2.5% by weight of the total weight of said solid particles and said impregnant.

* * * * *

UNITED STATES PATENT AND TRADEMARK OFFICE
CERTIFICATE OF CORRECTION

PATENT NO. : 5,955,109
DATED : Sep. 21, 1999
INVENTOR(S) : Won et al.

It is certified that error appears in the above-identified patent and that said Letters Patent is hereby corrected as shown below:

Claim 10, at column 16, line 2 "2.5" should read -- 2.5% --.

Claim 14, at column 16, line 35 "microns" should read -- microns, --.

Claim 14, at column 16, line 38 "10 micron" should read -- 1.0 micron --.

Signed and Sealed this

Thirteenth Day of June, 2000

Attest:

Q. TODD DICKINSON

*Attesting Officer*     *Director of Patents and Trademarks*